United States Patent [19]

Blackburn

[11] Patent Number: 4,486,292

[45] Date of Patent: Dec. 4, 1984

[54] SUPPORT AND ANCHORING MECHANISM FOR MEMBRANES IN SELECTIVELY RESPONSIVE FIELD EFFECT DEVICES

[75] Inventor: Gary F. Blackburn, North Salt Lake, Utah

[73] Assignee: Critikon, Inc., Tampa, Fla.

[21] Appl. No.: 457,818

[22] Filed: Jan. 13, 1983

Related U.S. Application Data

[63] Continuation-in-part of Ser. No. 304,722, Sep. 23, 1981.

[51] Int. Cl.³ ............................................. G01N 27/46
[52] U.S. Cl. ..................................... 204/416; 204/418; 357/23; 357/25
[58] Field of Search ............... 204/416, 418, 419, 403; 427/82; 357/23 R, 23 MG, 25, 71

[56] References Cited

U.S. PATENT DOCUMENTS

| | | | |
|---|---|---|---|
| 3,410,778 | 11/1968 | Krasberg | 204/415 |
| 3,645,875 | 2/1972 | Record et al. | 204/429 |
| 4,020,830 | 5/1977 | Johnson et al. | 204/403 |
| 4,180,771 | 12/1979 | Guckel | 357/25 |
| 4,273,636 | 6/1981 | Shimada et al. | 357/25 |
| 4,302,530 | 11/1981 | Zemel | 427/82 |
| 4,305,802 | 12/1981 | Koshiishi | 204/418 |

OTHER PUBLICATIONS

Blockburn, "The Suspended Mesh Ion Selective Field Effect Transistor", Dec. 1981, pp. 1-22.
Blockburn, "The Suspended Mesh ISFET", Jan. 1982, pp. 1-5.

*Primary Examiner*—T. Tung
*Attorney, Agent, or Firm*—Audley A. Ciamporcero, Jr.

[57] ABSTRACT

In the formation of a chemically sensitive field effect device, prior to formation of the gate membrane, an aluminum pad is disposed over the gate, and a polyimide layer is disposed thereover. Photoresist and etching steps produce openings in the polyimide to form a gridwork which is anchored to the device on the periphery of the gate. The aluminum layer is etched completely away, forming a void defined by the suspended polyimide mesh on one side, and the gate insulator on the other. Polymeric membrane is formed in the void by insertion in liquid form.

2 Claims, 5 Drawing Figures

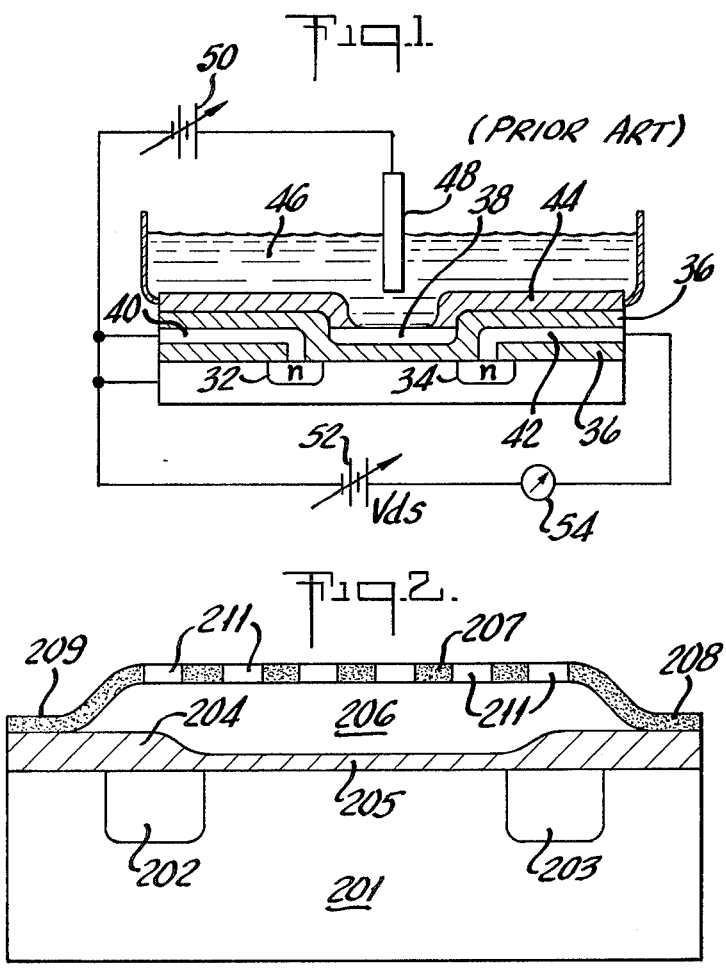
Fig. 1. (PRIOR ART)
Fig. 2.
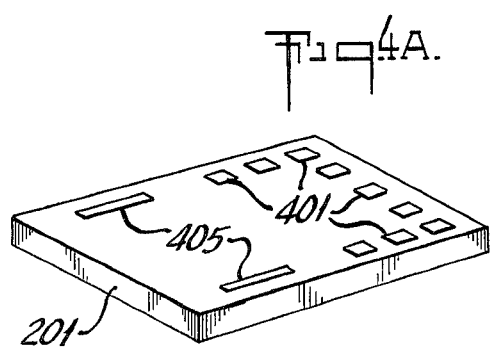
Fig. 4A.

SUPPORT AND ANCHORING MECHANISM FOR MEMBRANES IN SELECTIVELY RESPONSIVE FIELD EFFECT DEVICES

CROSS REFERENCE TO RELATED APPLICATION

This is a continuation-in-part of U.S. application Ser. No. 304,722 filed Sept. 23, 1981, entitled SUPPORT AND ANCHORING MECHANISM FOR MEMBRANES IN SELECTIVELY RESPONSIVE FIELD EFFECT DEVICES.

FIELD OF THE INVENTION

This invention relates to semiconductor devices whose electrical characteristics are dependent on the selective interaction of a portion thereof with specified substances, and more particularly to methods and apparatus whereby the selectively reactive region constitutes a membrane which is well-anchored in position thereover.

BACKGROUND OF THE INVENTION

There exists a class of devices exemplified by U.S. Pat. No. 4,020,830 to Johnson et al., dated May 3, 1977, entitled SELECTIVE CHEMICAL SENSITIVE FET TRANSDUCERS, which features electrical characteristics modulated by the interaction of a chemically selective system to specified ambient materials. In accordance with the Johnson patent, a substrate layer carries respective drain and source regions, separated by a region or channel over which is disposed an insulating layer and a chemically selective system for specified interaction with predetermined ambient materials. The chemically selective system generally takes the form of a membrane which interacts with the materials, and modulates the drain to source electrical conduction based on concentrations of the specified ambient substances. The Johnson et al. patent contemplates chemically selective systems for measuring various types of ambient conditions, including gas concentrations, ion activity, immunochemical concentrations, concentrations of enzymes and substrates, and the like, and indeed many such applications have found favor in a variety of disparate fields. While the nomenclature in the art has tended to designate these respective applications separately, for example utilizing the designation CHEMFET for chemically selective membrane devices, ISFET for ionically reactive devices, IMMUNOFET for immunologically reactive devices, and so forth, for purposes of this application the term "chemfet", or simply "device" shall be utilized generically to encompass all such apparatus, irrespective of the type of sensing or reaction utilized, character of the membrane employed, or nature of the ambient substance to be monitored. Likewise, the terms chemfet or device as used herein shall embrace transistor-type, diode-type, or the like other devices which feature similar conductivity modulation based on membrane-substance interaction.

In recent times, much effort has been expended in the development of device configurations and manufacturing processes which will facilitate large-scale production of reliable, stable, and well-calibrated devices. For example, device encapsulation, membrane formulation, and membrane disposition have proven to be formidable technical problems.

It is a general object of the present invention to provide device configurations and manufacturing processes for the production of superior chemfet devices, which have high reliability, well quantified specifications, suitable physical integrity, and a reasonable operational lifespan. With particular reference to the membrane aspect of the devices, it is to be noted that problems have been encountered both in the fabrication phase, and in the use and lifespan aspects of the devices. For example, polymeric membranes with high plasticizer content have found favor in the field, but production yield, operational reproducability, and physical integrity have all too often characterized the devices. Obviously, a chemfet membrane which is inadequately adhered to the gate insulator at the time of production will result in, at best, a gradual detachment of the membrane from the surrounding encapsulation. This results not only in a progressive loss of chemical response, but sooner or later in total failure of the device.

Accordingly, more specific objects of the present invention relate to provision of mechanisms, systems, and techniques whereby chemfet membranes are reliably, certainly, and substantially permanently attached to the device, thereby achieving superior mechanical integrity, and improved, well-characterized electrochemical operation.

It is a further specific object of the present invention to provide methods and structures whereby the devices may be effectively manufactured and encapsulated (i.e. hermetically sealed except for the controlled exposure of the gate area), without undue damage either to the gate membrane area, or to the device at large.

SUMMARY OF THE INVENTION

The principles of the present invention are premised upon the positioning of a suspended mesh of nonreactive material over the gate-membrane system, which anchors the membrane to the insulator, but through which the membrane reacts with ambient materials in substantially unimpeded fashion. In accordance with more particular aspects of the present invention, such a suspended mesh is built onto the device chip prior to application or formation of the membrane, and hence serves as a mechanism for the very formation of the membrane, as well as a superstructure to contain and anchor the membrane during the useful life of the device.

In a preferred form of the principles of the present invention, a chemfet device has a mesh grid of polyimide suspended above the gate insulator region of the device, supported by attachments about the periphery of the gate insulator area. Polymeric membrane material, in liquid form, may thus be deposited onto the mesh, thereby to wick into the void between the mesh and the insulator, with the balance to be cured over the mesh, or evaporated away. Upon suitable curing of the membrane, the mesh forms a support anchor and enclosure for the membrane.

In a preferred method of producing such devices, the formation of the grid is interposed as a series of processing steps during the basic device fabrication, preferably a wafer at a time. In particular, during the wafer processing, at the time at which aluminum bonding pads are deposited onto the chips, so also is an aluminum coating deposited over the insulated gate area of the device. The gate-insulator-aluminum area, and at least a boundary thereabout, is coated with polyimide, and thereupon utilizing photoresist etching techniques, a gridwork of openings is formed through the polyimide, down to the aluminum. Next, again utilizing photoresist-etching techniques, the aluminum beneath the polyimide is etched away, leaving a polyimide mesh suspended above the gate insulator, supported at the region surrounding the gate area. The void formed between the polyimide mesh and the gate insulator therebeneath forms the locus of the active membrane, which in operation will react with surrounding ambient materials through the openings in the polyimide grid mesh.

It will be appreciated, therefore, that in accordance with the principles of the present invention, more or less standard integrated circuit processing steps and materials are utilized synergistically, with a relative minimum of additional processing steps, to produce a chemfet device which largely avoids the problems conventionally attendant to membrane disassociation and consequent functional and electrical degredation and failure. Moreover, utilization of polyimide as the mesh provides an excellent biocompatible interface, allowing for efficient use of the devices in the close tolerance, very demanding environment of biomedical applications.

In accordance with alternative methods embodying the principles of the present invention, a non-reactive (e.g. polyimide) layer is formed over an aluminum deposit on the gate area, and then is provided with a layer of photoresist or aluminum, whereupon the devices are encapsulated. Thereafter, the individual chips are processed to remove the aluminum, and to yield a chip which has a full protective encapsulation except for the mesh, which itself has been protected by the aluminum during the separation and encapsulation process. The member or the gate may then be applied, and the device is ready for utilization.

DESCRIPTION OF THE DRAWINGS

FIG. 1 shows a cross-section of a prior art chemfet device;

FIG. 2 shows an illustrative embodiment of the principles of the present invention;

FIG. 4A shows a symbolic version of a two-device chemfet chip; and

DETAILED DESCRIPTION AND BEST MODE

Figure 4B:
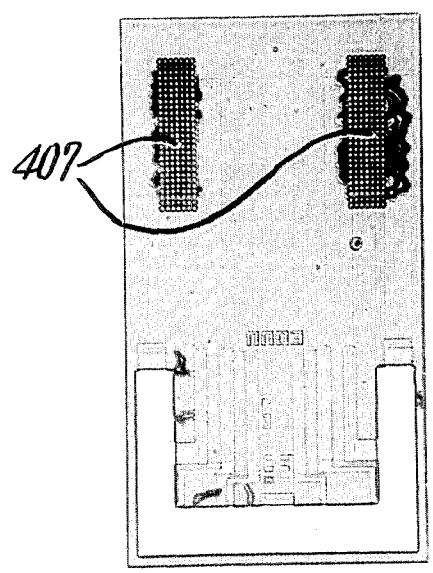
FIG. 4B shows a top view of such a chip incorporating the principles of the present invention.
Figure 3:
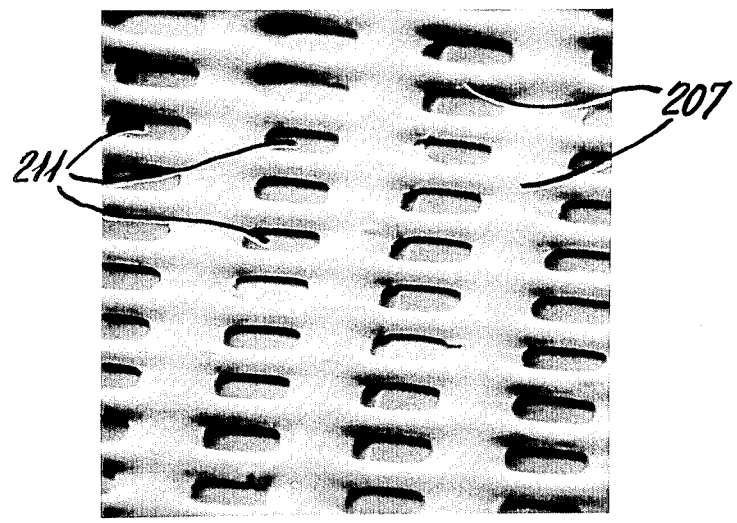
FIG. 3 shows a suspended mesh gate membrane anchor in accordance with the principles of the present invention.

Referring first to FIG. 1, there is shown a prior art depiction of a chemfet style device. In particular, the FIG. 1 device represents FIG. 2 of the previously cited U.S. Pat. No. 4,020,830 to Johnson, et al. In FIG. 1, a substrate 30 has diffused therein regions 32 and 34 which define the source and drain regions of the device. Layers of insulator 36 protect the device from ambient conditions, and conductor paths 40, 42 provide for electrical connection of the drain and source electrodes 32 and 34 to external circuitry. A membrane 38 overlays the gate region between the source and drain 32 and 34, and is held in place by a solution impervious layer 44. The solution or ambient substance 46 is in contact with the membrane 38, and a reference electrode 48, suitably biased with respect to the other terminals by circuitry 50 and 52, develops the desired reference voltage in order to enable operation of the device.

With reference next to FIG. 2, there is shown an illustrative embodiment of the principles of the present invention, wherein a polyimide grid mesh 207 is applied over the gate area of the device. In particular, in FIG. 2, a substrate 201 has diffused therein respective drain and source regions 202 and 203. It will be appreciated that in the embodiment of FIG. 2, the actual electrical interconnection of the drain and source electrodes to the exterior (i.e. the symbolic connections 40, 42 of FIG. 1) are not shown, it being understood that in the actual pattern of the device (e.g. as discussed herein in conjunction with FIGS. 4A and 4B) will be considerably more elaborate than shown in FIG. 2. In any event, in FIG. 2, an insulator layer 204 is deposited, and intermediate the drain and source 202 and 203, forms a gate or channel region 205, the conductivity of which is to be modulated by the interaction of an overlying chemically selective membrane with ambient materials. The area 206 directly above the gate insulator region 205 is the location for application of a membrane, but in accordance with the principles of the present invention, as distinct from the prior art exemplified in FIG. 1, it is desirable first to fabricate a suspended grid mesh 207, above the gate insulator region 205, forming the void 206 into which the membrane is later formed. As noted in FIG. 2, the suspended mesh 207 is coupled to the device, and more particularly to the insulator layer 204, about the periphery of the gate insulator region, for example as shown at 208 and 209. The suspended mesh 207 defines openings 211 therethrough, through which the membrane to be located at 206 will interact with the ambient materials in selective fashion.

A preferred method of fabricating devices of the sort shown in FIG. 2 is as follows, it being understood that incorporation of the principles of the present invention is quite compatible with fabrication of more conventional type chemfet devices, entailing the addition of some intermediate process steps, the character of which are synergistic with, and at times partially overlapping with the conventional processing steps. It is to be further understood that the most advantageous time of incorporating the principles of the present invention is in the fabrication of an entire wafer of devices, although for illustrative purposes, the drawings in discussion herein relate only to a single device.

After the device is completed through application of the insulating layer 204 and 205 of the devices, aluminium is deposited over the entire wafer, for example by vacuum deposition. At this point, conventional processes call for the etching of all aluminium from the wafer except at the bonding pads and, if any, the conduction paths. In accordance with the principles of the present invention, however, the etching-photoresist masks are arranged to maintain a coating of aluminum (e.g. one micron thick) over the gate area 205 of each chip.

Next, conventional fabrication techniques would call for application of an impervious layer (e.g. 44 in FIG. 1). In a preferred embodiment of the present invention, a layer of polyimide is spun over the device, for example to a thickness of 1,000 angstroms. The polyimide layer is set, for example by pre-baking, and a photoresist masking process exposes scribe lines and bonding pads, as in the case of the more conventional procedures, and also a gridwork or mesh of spots (211 in FIG. 2) atop the aluminum pad which at this point still covers the gate insulator area.

Thereupon, utilizing conventional photoresist techniques, the polyimide is etched away over the bonding pads, from the scribe lines, and, most importantly from the standpoint of the principles of the present invention, from the gridwork of holes 211 over the aluminum-gate insulator layer. As desired, the polyimide is then rinsed and subjected to post-baking, to promote setting. In accordance with the principles of the present invention, the aluminium layer under the recently formed mesh is to be etched away, and accordingly photoresist is deposited over the aluminium bonding pads to prevent them from also being etched away. Thereupon, the aluminum from underneath the polyimide mesh is etched away completely (for example utilizing a solution of acetic acid, nitric acid, and phosphoric acid), until there is defined the void area 206 shown in FIG. 2 between the now suspended mesh 207 and gate insulator area 205 therebeneath.

The photoresist is removed from the bonding pads, the device is suitably dried and cleaned, and at this point conventional processing of the wafer, as desired, is continued.

With reference to FIG. 2, there is shown a representation of a preferred form of a suspended mesh structure 207, with the openings 211 having been formed therein. In a preferred embodiment, the mesh 207 is suspended approximately one micron above the gate insulator. The openings are in the range of approximately ten microns by ten microns, and separated in respective dimensions by comparable amounts. As the device is first fabricated, the void 206 is filled only by air. In order to form a membrane in the void, one may simply place a drop of the membrane material in liquid form (e.g. polymeric material deposited utilizing a syringe), which wicks through the openings 211 in the suspended mesh, fills the void 206, and upon curing forms the membrane. In one embodiment, the excess liquid is evaporated off. In another, the membrane is formed over as well as under the mesh.

Referring finally to FIGS. 4A and 4B, there is shown somewhat symbolically the application of the principles of the present invention to a two device chip. In particular, the chip 201 of FIG. 4A represents a sort of semiconductor chip which is known to be practicable, each chip 201 including two separate chemfet devices. The bonding pads 401 to the chip are shown spaced away from the gate insulator areas 405 of the respective devices. As noted in FIG. 4B, respective polyimide suspended meshes 407 are disposed over the completed chip, with the balance of the devices clustered at the opposite end thereof.

It is clear that in any event, prior to use the chemfet-style devices must be encapsulated, whereby the gate/-membrane area of the device is the only exposed area, while the remainder of the device is hermetically encapsulated and sealed from the ambient environment. In one class of encapsulation techniques, as embodied in U.S. application Ser. No. 338,732 to Kratochvil et al., filed Jan. 11, 1982, entitled "System for Encapsulation of Semiconductor Chips Devices" photoresist techniques for selection application of reston windows or chimneys above the gate area allow for encapsulation of the device while the devices are still coupled to one another in water form. In an alternative class of encapsulation techniques, the various devices on a wafer are separated into individual chips, which are respectively encapsulated utilizing tape automated bonding procedures. This latter class is exemplified by U.S. patent application Ser. No. 350,929 of Kratochvil et al. filed Jan. 18, 1982, entitled "Method and Apparatus for Encapsulation of Chemically Sensitive Field Effect Device". It is contemplated that in accordance with the principles of the present invention, either such encapsulation technique may be utilized. Further, to the extent appropriate, both of the foregoing patent applications are incorporated by reference herein.

In accordance with an alternative embodiment of the principles of the present invention, suspended mesh devices are encapsulated prior to the etchant removal of the aluminum spacer from underneath the suspended mesh. Such an approach has distinct advantages. First, since the device has been encapsulated by the time of removal of the aluminum from beneath the mesh, the aluminum bonding pads on the chip (which are applied at the same time as the aluminum over the gate area) are not exposed to the etching solution or process. This is in contrast to those embodiments wherein the bonding pads must be protected (e.g. by photoresist), while the aluminum is being removed from beneath the suspended mesh. In accordance with the instant alternative embodiment, since the encapsulation has occurred, this extra photoresist step of protecting the bonding pads is obviated. Thus, by etching the aluminum from beneath the suspending mesh after encapsulation, the total device processing effort is reduced by at least 10-20%.

Another advantage of the alternative embodiment is overall integrity and protection of the structure. That is, if the aluminum from beneath the suspended mesh is removed prior to separation and encapsulation of the chip, it is possible that the suspended mesh could be subjected to damage during dicing of the wafer, and handling and transfer of the individual chips during encapsulation. In contrast, maintenance of an aluminum support structure under the mesh during such dicing, handling, transfer, and encapsulation obviously avoids such damage.

Furthermore, utilization of the instant alternative embodiment provides further protection for the silicon nitride surface of the gate area of the device. That is, if the aluminum from beneath the suspended mesh is removed early in the process, there exists a path whereby corrosive or physical damage may result to the gate area itself. For example, thin layers of organic material may coat the gate area of the unprotected device during the encapsulation process. These layers may be materials which leached out of the encapsulant during curing, or may be contaminants from other sources. In any event, there results a diminished electrochemical device response. These effects are avoided if the device includes aluminum under the mesh but coating the gate during the dicing, handling, and encapsulation steps.

In preferred embodiments, the suspended mesh may be composed of either of the two polyimide polymers commercially available from duPont, under the respective trade designations "PI-2540" or "PI-2550". In fact, the difference between the two polymers is believed small and to have minimal effect on the operation or fabrication of the suspended mesh. Nevertheless, to the extent the one seems preferable over the other, the latter polymer is the one of choice.

In one embodiment, photoresist is used as the mask to define the holes in the polyimide mesh. In such procedure, after etching of the holes through the polyimide, the wafer is placed in a 300° C. oven fully to cure the polyimide. In such instance, the suspended mesh formed over the gate is on the order of one micron thick.

In an alternative embodiment, aluminum is used as a mask for removal of the openings through the suspended mesh. Utilizing such a technique, there does indeed result a mesh of approximate thickness of 1,000 Angstroms.

Nevertheless, regardless of whether photoresist or aluminum masking is utilized for formation of openings in the mesh, there does result a suspended mesh which appears functionally to be adequate. Depending upon the desires of the designer, and the ultimate thickness and strength of mesh which is desired, it is possible either to use the mesh alone for formation of the membrane, or, during the step of etching removal of the aluminum from beneath the mesh, to remove less than all of the aluminum and to produce aluminum support "columns" or "pillars" to support the mesh above the gate area.

Hence, devices in accordance with alternative methods may be prepared by applying aluminum over the gate at the same time as bonding pads and applied, and coating the aluminum with polyimide which adheres to the device around the aluminum. The mesh structure in the polyimide may then be formed, or the mesh pattern may then be formed for later removal of the mesh areas. The device is further processed and encapsulated as desired, whereupon the mesh pattern is etched, and some or all of the aluminum is removed from beneath the mesh. The thin band is formed, and the device is ready for use.

It will be appreciated that the foregoing sets forth preferred and illustrative embodiments of the principles of the present invention, but that numerous alternative embodiments will occur to those of ordinary skill in the art, without departure from the spirit or scope of the present invention. For example, it is not contemplated that the principles of the present invention are limited to a specific composition of the suspended mesh (other polymers or other materials may be substituted for the polyimide) nor specific dimensions. The fabrication processing steps set forth are in large respect characteristic of the state of the art of semiconductor fabrication, but the specific aspects of photoresist-etching, and curing as well as selection of materials, will no doubt advance with time, and it is to be anticipated that the principles of the present invention may be applied even with greater facility to the newer processing techniques. Finally, it is to be anticipated that devices which employ different overall forms, such as different junction configurations between input and output (e.g. single or multiple junction devices) will be perfectly amenable to application of the principles of the present invention, to the extent that such devices employ a gate style membrane of the sort discussed herein.

I claim:

1. In a system employing a selectively reactive membrane overlying a specified gate region of a field effect device, the improvement comprising: a substantially nonreactive mesh structure spaced away from but overlying said specified region, wherein said mesh spans and encloses said gate region, is affixed to said device about the periphery of said region, and forms a void, open through said mesh, for location of a membrane; and a membrane integrally located within said void and through openings in said mesh on the outside of said mesh.

2. The invention described in claim 1 wherein said mesh consists essentially of polyimide material.

* * * * *